United States Patent [19]

Carr et al.

[11] 4,091,221
[45] May 23, 1978

[54] 3-(BENZOYL)OXIRANECARBOXAMIDES

[75] Inventors: John B. Carr; Harry G. Durham, both of Modesto, Calif.

[73] Assignee: Shell Oil Company, Houston, Tex.

[21] Appl. No.: 778,536

[22] Filed: Mar. 17, 1977

[51] Int. Cl.$^2$ .................. C07D 413/02; C07D 303/36
[52] U.S. Cl. ........................... 544/147; 424/248.51; 424/248.54; 424/248.57; 424/267; 424/274; 424/278; 260/293.67; 260/326.36; 260/326.5 SF; 260/326.5 D; 260/348.43; 260/348.45; 260/348.46; 260/348.47

[58] Field of Search ................. 544/147; 260/293.67, 260/348.43, 348.45, 348.46, 326.36, 326.5 SF, 326.5 D, 348.47

[56] References Cited

U.S. PATENT DOCUMENTS 2,850,509  9/1958  Nichols et al. ............... 260/348.46

Primary Examiner—Henry R. Jiles
Assistant Examiner—R. W. Ramsuer

[57] ABSTRACT

Novel trans-isomers of 3-(benzoyl)oxiranecarboxamides, useful as lipogenesis inhibitors in warm-blooded animals.

1 Claim, No Drawings

3-(BENZOYL)OXIRANECARBOXAMIDES

DESCRIPTION OF THE INVENTION

It has been found that lipogenesis in warm-blooded animals is inhibited by the trans-isomeric form of 3-(benzoyl)oxiranecarboxamides of the formula:

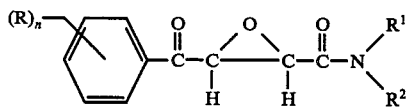

wherein $n$ is zero, one, two or three, R is halogen nitro, trifluoromethyl, alkyl, alkoxy, alkanoyl or alkamido in which the alkyl moities thereof contain from one to six carbon atoms, methylsulfonyl, methylsulfonylamino, or halobenzoyl and $R^1$ and $R^2$ each is hydrogen or alkyl, alkenyl or alkynyl of up to sixteen carbon atoms, or together are $-(CH_2)_4-$, $-(CH_2)_5-$ or $-C_2H_4-O-C_2H_4-$.

In these compounds, each alkyl, alkenyl and alkynyl moiety suitably can be either straight-chain or branched-chain in configuration. Preferably, each such moiety contains no more than three carbon atoms. The terms "halogen" and "halo" designate bromine, chlorine, fluorine or iodine, middle halogen — i.e., bromine and chlorine — being preferred.

Because of the manner in which they are prepared, compounds of the invention are in the form of the trans isomers.

Further, chirality exists in the compounds of Formula I due to the asymmetric structural configurations at the 2- and 3-postions of the oxirane ring. As a result, two optical isomers of the trans isomers of Formula I exist. At the time this application is filed, no attempt has been made to separate and determine the lipogenesis inhibition activity of the individual optical isomers. Under the circumstances, the invention contemplates the individual optical isomers, as well as mixtures thereof.

For illustration, preparation of typical individual species of the genus defined by formula (I) are described in the examples included hereinafter. Other typical, illustrative individual species of this genus are those wherein the respective moieties, R, $R^1$ and $R^2$ are:

| R | $R^1$ | $R^2$ |
| --- | --- | --- |
| 4-fluoro | H | H |
| 4-bromo | H | H |
| 4-methylsulfonyl | H | H |
| 4-methoxy | H | H |
| 4-trifluoromethyl | H | H |
| 4-acetamido | H | H |
| 4-methylsulfonylamino | H | H |
| 4-acetyloxy | H | H |
| 3-nitro | H | H |
| 4-chloro | $(-C_2H_4-O-C_2H_4-)$ | |
| 4-chloro | H | 2-propenyl |
| 4-chloro | H | 2-propynyl |
| 2,4-dichloro | H | H |
| 4-chloro | H | lauryl |
| 2,4,5-trichloro | H | propyl |
| 3-trifluoromethyl | H | H |
| 4-(4-chlorobenzoyl) | H | H |

Compounds of this genus can be prepared by treating the appropriate 3-(benzoyl)acrylamide with a moderate excess of hydrogen peroxide in the presence of a catalytic amount of a base (about 2-5% based on the number of moles of the acrylamide), such as sodium hydroxide, in a suitable solvent such as ethanol, which may contain a minor amount of water, at moderately elevated temperature, as, for example, from 40° to 60° C.

The acrylamide can be prepared by treating the appropriate 3-(benzoyl)acrylic acid with a slight (5-20%) excess of phosphorus pentachloride in a suitable liquid medium (for example, a haloalkane, such as methylene chloride), at a moderately elevated temperature (for example, about 40° C, the boiling point of methylene chloride), to form the acid chloride, which then can be converted to the amide by treatment with ammonia or the appropriate amine, $H-NR^1R^2$, suitably in a solvent such as benzene or toluene at a low temperature, for example, −5° to 10° C, then if necessary to ensure complete reaction, warming the mixture and holding it at room temperature or somewhat above - for example, 30°-40° C.

Alternatively, the acrylamide can be prepared as follows: a mixed anhydride can be prepared by treating the acrylic acid with ethyl chloroformate in the presence of a tertiary amine, such as triethylamine, in a suitable liquid reaction medium, such as chloroform or toluene, at a low temperature — for example, −5° to 10° C — then warming and holding the mixture at room temperature or somewhat above to ensure complete reaction. The resulting mixed anhydride is then treated with ammonia or the appropriate amine to form the amide.

Most of the acrylic acid precursors can be prepared by the Friedel-Crafts acylation of the appropriate benzene compound, $(R)_n$ benzene, with maleic anhydride, according to the method of D. Papa, et al., J. Am. Chem. Soc., 70, 3356 (1948). The precursor for (3-trifluoromethyl)benzoylacrylic acid was prepared from (3-trifluoromethyl)acetophenone and glyoxylic acid, according to the procedure described in U.S. Pat. No. 3,753,997.

The procedures for preparing compounds of Formula I are illustrated in Examples 1-11, following. In each case, the identities of the product, and of the precursor(s) involved were confirmed by appropriate chemical and spectral analyses.

EXAMPLE 1

3-(4chlorobenzoyl)oxiranecarboxamide(trans) 1

3-(4-chlorobenzoyl)acrylic acid (1A) was prepared, as a yellow crystalline solid, m.p.: 157°-158° C, by the Friedel-Crafts acylation of chlorobenzene with maleic anhydride by the method of Papa et al., J. Am. Chem. Soc., 70, 3356 (1948).

To a slurry of 21 g of 1A in 100 ml of methylene chloride was added 21 g of phosphorus pentachloride. The resulting homogenous yellow solution was stripped at 40° C and the resulting residue was extracted with benzene. Cooling of the benzene solution gave the corresponding acid chloride (1B), m.p.: 96°-97° C. 1B was dissolved in 100 ml of benzene and ammonia gas was passed into the solution. The temperature of the reaction mixture rose from 30° to 55° C. A precipitate that formed was separated and washed with water, and the remaining solid was recrystallized from chloroform to give 3-(4-chloro-benzoyl)acrylamide (1C) as a white crystalline solid, m.p.: 172° C (with decomposition).

A solution of 3.7 g of 1C, 4 ml of 30% hydrogen peroxide and 5 ml of 0.1 N aqueous sodium hydroxide in 100 ml of methanol was heated to 50° C and then allowed to cool to 25° C over a period of two hours. A precipitate that formed was separated and washed with ethanol to give 1, as a white solid, m.p.: 218°–219° C.

EXAMPLE 2

3-(4-chlorobenzoyl)-N,N-dimethyloxiranecarboxamide(trans) (2(2)

A solution of 21 g of 1A in 200 ml of chloroform was cooled to 0° C. 14 ml of triethylamine was added, then 300 ml of toluene was added. To that mixture held at 10° C, 10 ml of ethyl chloroformate was added dropwise. The temperature of the final mixture was then raised to 20° C and held there for one hour. The mixture then was cooled to 10° C and held at 0°–10° 1 C while a solution of 5 g of dimethylamine in 100 ml of toluene was slowly added. Gaseous dimethylamine then was passed into the mixture until no heat of reaction was noted. The mixture was filtered. The filtrate was stripped of solvent to give a solid product, which was dissolved in methylene chloride. The solution was washed with water, the solvent was evaporated, and the product was recrystallized from ethyl acetate to give the corresponding N,N-dimethyl amide (2A), as a yellow solid, m.p.: 117°–118° C.

2 prepared as a white solid, m.p.: 103°–104° C, by peroxide oxidation of 2A, by the procedure described in Example 1.

EXAMPLE 3

3-(4-chlorobenzoyl)-N-methyloxiranecarboxamide (3)

3 was prepared as a white solid, m.p.: 160°–161° C, from 4-(4-chlorophenyl)-N-methyl-4-oxo-2-butenamide (3A) by hydrogen peroxide oxidation by the procedure described in Example 1, 3A having been prepared from the corresponding acrylic acid and monomethylamine by the procedure described in Example 2.

EXAMPLE 4

3-(3,4-dichlorobenzoyl)oxiranecarboxamide (4)

28 ml of triethylamine was dissoved in 600 ml of cloroform, then 49 g of 3-(3,4-dichlorobenzoyl)acrylic acid was added. The resulting solution was cooled to 0° C, and 42 g of ethyl chloroformate was added. The mixture was warmed to 20° C, stirred for one hour, cooled to 0° C and then held there while gaseous ammonia was passed into the solution until no further heat of reaction was noted. A precipitate that formed was collected, washed with water and then with acetone to give 4-(3,4-dichlorophenyl)-4-oxo-2-butenamide (4A), as a white solid, m.p.: 208° C (with decomposition).

4 was prepared, as a white solid, m.p.: 165°–167° C, by hydrogen peroxide oxidation of 4A by the procedure described in Example 1.

EXAMPLES 5 and 6

By the procedures described in Example 4, there was prepared from the appropriate precursors:
3-(4-methylbenzoyl)oxiranecarboxamide (5), as a white solid, m.p.: 209°–210° C, and
3-(benzoyl)oxiranecarboxamide (6), as a white solid, m.p.: 174°–175° C.

EXAMPLE 7

3-(4-chlorobenzoyl)-N-(1-methylethyl)oxiranecarboxamide (7)

The precursor 4-(4-chlorophenyl)-N-(1-methylethyl)-4-oxo-2-butenamide (7A) was prepared by the procedure shown in the previous examples by treating 1A with ethylchloroformate and triethylamine in toluene at 0°, then adding at 0° a solution of isopropylamine in toluene. 7A was obtained as a solid, m.p.: 162°–163°. It was converted to 7 by treatment with hydrogen peroxide, by the procedure described in Example 1, 7 being obtained as a solid, m.p.: 128–129°.

EXAMPLE 8

3-(3-nitrobenzoyl)oxiranecarboxamide 8

22 g of finely powdered 3-benzoylacrylic acid was added in 1-gram portions to 11° g of stirred fuming (90%) nitric acid at −5° over a 30-minute period, the mixture being allowed to heat to 0°. Then the temperature of the mixture was allowed to rise to 2° and held until a clear solution was obtained. The mixture then was poured on ice, and the solid which formed was filtered, washed with water, dried (MgS0$_4$) and recrystallized from ethanol to give 3-(3-nitrobenzoyl)acrylic acid (8A), m.p.: 199°–201°.

8A was treated with ammonia, according to the procedure described in Example 2, to give the corresponding amide (8B).

8B was converted to 8, a solid, m.p.: 165°–167°, by treatment with hydrogen peroxide according to the procedure described in Example 1.

EXAMPLE 9

3-(4-chlorobenzoyl)-N-(2-propenyl)oxiranecarboxamide (9), was prepared as a solid, m.p.: 108°–117°, from 1A and allylamine by the procedures described in Example 4.

EXAMPLE 10

(4-chlorophenyl)-3-(4-morpholinylcarbonyl)oxiranyl)methanone (10) was prepared as a solid, m.p.: 137°–139°, from 1A and morpholine by the procedures described in Example 4.

EXAMPLE 11

3-(4-acetamidobenzoyl)oxiranecarboxamide (11)

A finely powdered mixture of 50 g of acetamide and 38 g of maleic anhydride was added over a 2-minute period to a stirred slurry of 185 g of aluminum chloride in 250 ml of carbon disulfide at 0°, allowing the mixture temperature to rise to 35° and stirred for 4 hours. The mixture was allowed to stand for 72 hours, then it was broken up and added in small portions to a mixture of ice and 6N hydrochloric acid. The solid which formed was filtered and boiled with ethanol; the mixture was filtered. The filtrate was cooled and filtered to give 3-(4-acetamidobenzoyl)acrylic acid (11A), m.p.: 220°–225°.

11A was converted to 11 as a white solid, m.p.: 206°–207°, by the procedures described in Example 4.

The carboxamides of Formula I have been found to inhibit lipogenesis in tissues of warm-blooded animals, particularly mammals. The manner in which they cause this effect is not known with certainty; it is believed that they interfere with the synthesis of fatty acids in the tissues. Their effectiveness for this purpose has been ascertained by immersing samples of animal liver or adipose tissue in a liquid medium containing radioactive glucose and the test chemical, for a period of time, then isolating the lipid from the treated tissued and determining the up-take of the radioactive carbon by means of scintillation counting techniques. These tests were conducted in both liver and adipose tissue, because in some animals the primary site of lipogenesis appears to be liver tissue, while in others it appears to be adipose tissue. The test animals were pigs, chickens and sheep.

Described in more detail, the tests were conducted according to the following general procedure:

Tissue slices (200 miligrams for liver and 150 milligrams for adipose tissue) were incubated at 37° C for 2 hours with shaking in 3 milliliters of Krebs-Ringer bicarbonate solution containing one-half the normal calcium ion concentration, 60 micromoles of glucose, 0.5 micro-Curie of glucose-$U^{14}C$, and 300 microunits of insulin, and 5% dimethyl sufoxide (DMSO). The test compounds were added as a suspension in DMSO and were present at a concentration of 100 micrograms per milliliter of the incubation mixture.

The incubation was terminated by addition of 0.25 milliliter of 1 N sulfuric acid. The resulting mixture was extracted with a total of 25 milliliters of chloroform: methanol (2:1, v/v). The extracts were washed according to Folch et al. (J. Biol. Chem., 226, 497–509, (1957)), air dried, and counted in a liquid scintillation counter with 15 milliliters of counting fluid (two parts toluene containing 0.4% w/v New England Nuclear Omnifluor: 1 part Triton X-100). The tests were conducted in triplicate and were accompanied by control tests in which all ingredients, proportions and conditions were the same except that no test compound was included. From the data obtained were calculated the percent inhibition of lipid synthesis by the test compounds in each case.

Compound 1 was tested with respect to all of the animals. The other compounds were tested only with respect to the pig.

From these and other tests, it has been established that in pigs there is little lipogenic activity in the liver tissue. From these and other tests, it also has been established that swine adipose tissue utilizes glucose for lipogenesis, and to be the major site of fatty acid synthesis. The data obtained from the tests using adipose tissue and glucose are set out in Table 1, as the percent inhibition of lipogenesis compared to the results obtained in the control tests wherein only the test compound was omitted.

TABLE I

| Compound No. | Percent Inhibition |
|---|---|
| 1 | 94 |
| 2 | 70 |
| 3 | 96 |
| 4 | 96 |
| 5 | 89 |
| 6 | 91 |
| 7 | 90 |
| 8 | 96 |
| 9 | 94 |
| 10 | 77 |

With respect to chickens: the primary site of fatty acid synthesis is the liver. Compound 1 inhibited glucose incorporation into the liver by 54%.

With respect to sheep, the liver incorporated more glucose into lipids than did the adipose tissue. Compound 1 inhibited (10%) glucose incorporation in the liver and (65%) in adipose tissue.

The carboxamides of Formula I can be used to control lipogenesis in warm-blooded animals such as, for example, pets, animals in a zoo, livestock, fur-bearing animals and domestic animals, including, but not limited to dogs, cats, mink, sheep, goats, swine, cattle, horses, mules, donkeys and poultry. The effect is obtained by administering an effective amount of one or a mixture of two or more of the carboxamides orally or parenterally to the animal. They may be administered as such, or as an active ingredient of a conventional pharmaceutical formulation. They may be administered orally by any convenient means. Thus, they may be orally administered as a drench, by intubation, in the animal's food and water, in a food supplement or in a formulation expressly designed for administration of the drug. Suitable formulations include solutions, suspensions, dispersions, emulsions, tablets, boluses, powders, granules, capsules, syrups and elixirs. For parenteral administration, they may be in the form of a solution, suspension, dispersion or emulsion. They can be administered in the form of an implant or other controlled sustained release formulation. Inert carriers, such as one or more of water, edible oil, gelatin, lactose, starch, magnesium stearate, talc or vegetable gum can be used. The dosage of the carboxamide needed to inhibit lipogenesis will depend upon the particular carboximide used, and the particular animal being treated. However, in general, satisfactory results are obtained when the carboxamides are administered in a dosage of from about 1 to about 500 milligrams per kilogram of the animal's body weight. The carboxamide can be administered in a single dose or in a series of doses in the same day, or over a period of days. For any particular animal, a specific dosage regimen should be adjusted according to the individual need, the particular carboxamide(s) used as the inhibitor, and the professional judgment of the person administering or supervising the administration of the inhibitor. It is to be understood that the dosages set forth herein are exemplary only, and that they do not, to any extent, limit the scope or practice of the invention.

We claim:

1. A compound of the formula:

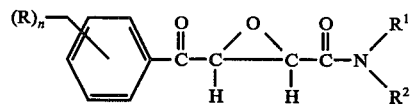

wherein $n$ is zero, one, two or three, R is halogen, nitro, trifluoromethyl, alkyl, alkoxy, alkanoyl or alkamido in which the alkyl moieties thereof contain from one to six carbon atoms, methylsulfonyl, methylsulfonylamino or halobenzoyl, $R^1$ and $R^2$ each is hydrogen or alkyl, alkenyl or alkynyl of up to sixteen carbon atoms, or together are $(CH_2)_4$, $(CH_2)_5$, or $-C_2H_4-O-C_2H_4-$, the compound having the trans-isomeric configuration.

* * * * *

UNITED STATES PATENT AND TRADEMARK OFFICE
CERTIFICATE OF CORRECTION

PATENT NO. : 4,091,221

DATED : May 23, 1978

INVENTOR(S) : JOHN B. CARR and HARRY G. DURHAM

It is certified that error appears in the above-identified patent and that said Letters Patent are hereby corrected as shown below:

Column 4, line 43 (first line of Example 11), change "acetamide" to -- acetanilide --.

Signed and Sealed this

Eleventh Day of September 1979

[SEAL]

Attest:

Attesting Officer

LUTRELLE F. PARKER

Acting Commissioner of Patents and Trademarks